United States Patent
Hosogoe

(10) Patent No.: US 12,144,490 B2
(45) Date of Patent: Nov. 19, 2024

(54) ENDOSCOPE

(71) Applicant: HOYA CORPORATION, Tokyo (JP)

(72) Inventor: Yoshitsugu Hosogoe, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 444 days.

(21) Appl. No.: 17/632,072

(22) PCT Filed: Dec. 25, 2020

(86) PCT No.: PCT/JP2020/048774
§ 371 (c)(1),
(2) Date: Feb. 1, 2022

(87) PCT Pub. No.: WO2021/140964
PCT Pub. Date: Jul. 15, 2021

(65) Prior Publication Data
US 2022/0273162 A1  Sep. 1, 2022

(30) Foreign Application Priority Data

Jan. 9, 2020 (JP) .................................. 2020-002242

(51) Int. Cl.
*A61B 1/005* (2006.01)
*A61B 1/00* (2006.01)

(52) U.S. Cl.
CPC .......... *A61B 1/005* (2013.01); *A61B 1/00078* (2013.01); *A61B 1/0055* (2013.01); *A61B 1/0057* (2013.01)

(58) Field of Classification Search
CPC .. A61B 1/00078; A61B 1/0055; A61B 1/0057
See application file for complete search history.

(56) References Cited

U.S. PATENT DOCUMENTS 4,329,980 A * 5/1982 Terada ................. A61B 1/0055
  600/140
4,977,887 A * 12/1990 Gouda ............... A61B 1/00071
  600/140

(Continued)

FOREIGN PATENT DOCUMENTS

JP  2002-355217  12/2002
JP  2004-230201   8/2004

(Continued)

OTHER PUBLICATIONS

International Search Report issued in International Bureau of WIPO Patent Application No. PCT/JP2020/048774, dated Mar. 23, 2021, along with an English translation thereof.

*Primary Examiner* — Aaron B Fairchild
*Assistant Examiner* — Stephen Floyd London
(74) *Attorney, Agent, or Firm* — GREENBLUM & BERNSTEIN, P.L.C.

(57) ABSTRACT

An endoscope includes: a hardness adjustment cable that is arranged in an insertion portion and includes a hardness adjustment sheath, a hardness adjustment wire inserted in the hardness adjustment sheath, and a coupling tool coupling the hardness adjustment sheath and the hardness adjustment wire; a retaining member fixed to the hardness adjustment wire on an operation unit side of the hardness adjustment cable; a cam mechanism that is coupled to the retaining member when tension is applied to the hardness adjustment wire; a sheath fixing unit coupled to the hardness adjustment sheath on the operation unit side of the hardness adjustment cable; and a guide frame that is arranged between the insertion portion and an operation unit and that holds the cam mechanism and the sheath fixing unit so as to be independently movable in a longitudinal direction of the insertion portion.

10 Claims, 17 Drawing Sheets

(56) References Cited

U.S. PATENT DOCUMENTS

| | | | |
|---|---|---|---|
| 6,203,494 B1* | 3/2001 | Moriyama | A61B 1/00078 |
| | | | 600/149 |
| 2002/0002323 A1* | 1/2002 | Moriyama | A61B 1/0051 |
| | | | 600/130 |
| 2007/0212913 A1* | 9/2007 | Takeuchi | A61B 1/0051 |
| | | | 439/188 |
| 2008/0200762 A1* | 8/2008 | Stokes | A61B 1/31 |
| | | | 600/114 |
| 2012/0071722 A1* | 3/2012 | Nakamura | A61B 1/0051 |
| | | | 600/140 |
| 2015/0087905 A1* | 3/2015 | Ueda | A61B 1/0057 |
| | | | 604/95.04 |
| 2017/0127910 A1 | 5/2017 | Asaoka et al. | |
| 2018/0035870 A1 | 2/2018 | Okaniwa et al. | |
| 2019/0082935 A1 | 3/2019 | Kitanaka | |
| 2019/0246885 A1* | 8/2019 | Karikomi | A61B 1/015 |
| 2020/0297188 A1* | 9/2020 | Ikeda | A61B 1/0053 |
| 2020/0323421 A1* | 10/2020 | Okaniwa | A61B 1/00135 |
| 2020/0352412 A1 | 11/2020 | Saito | |

FOREIGN PATENT DOCUMENTS

| | | |
|---|---|---|
| JP | 2017-086389 | 5/2017 |
| WO | 2017/086311 | 5/2017 |
| WO | 2017/203627 | 11/2017 |
| WO | 2019/150627 | 8/2019 |

\* cited by examiner

ENDOSCOPE

TECHNICAL FIELD

The present invention relates to an endoscope.

BACKGROUND ART

Endoscopes that can change the hardness of an insertion portion during an endoscopic examination have been proposed (Patent Literature 1 and Patent Literature 2).

CITATION LIST

Patent Literature

Patent Literature 1: JP 2004-230201 A
Patent Literature 2: JP 2002-355217 A

SUMMARY OF INVENTION

Technical Problem

In the endoscopes of Patent Literature 1 and Patent Literature 2, a hardness adjusting coil and a hardness adjusting wire inserted inside the hardness adjusting coil are used for a hardness adjustment mechanism inside the insertion portion. The hardness adjusting coil and the hardness adjusting wire are fixed to a distal tip side of the insertion portion. Only the hardness adjusting wire is pulled on an operation unit side to change the hardness of the insertion portion by utilizing the fact that the hardness adjusting coil is hardened by being compressed.

In the endoscopes of Patent Literature 1 and Patent Literature 2, however, tension or a compressive force is applied to the hardness adjusting coil and the hardness adjusting wire when the insertion portion is complicatedly curved, and thus, there is a case where it is difficult to obtain a sufficient effect even if a user operates the hardness adjustment mechanism.

In one aspect, an object of the invention is to provide an endoscope in which a hardness adjustment mechanism operates smoothly.

Solution to Problem

An endoscope includes: a hardness adjustment cable that is arranged in an insertion portion and includes a hardness adjustment sheath, a hardness adjustment wire inserted in the hardness adjustment sheath, and a coupling tool coupling the hardness adjustment sheath and the hardness adjustment wire; a retaining member fixed to the hardness adjustment wire on an operation unit side of the hardness adjustment cable; a cam mechanism that is coupled to the retaining member when tension is applied to the hardness adjustment wire; a sheath fixing unit coupled to the hardness adjustment sheath on the operation unit side of the hardness adjustment cable; and a guide frame that is arranged between the insertion portion and an operation unit and that holds the cam mechanism and the sheath fixing unit so as to be independently movable in a longitudinal direction of the insertion portion.

Advantageous Effects of Invention

In one aspect, it is possible to provide the endoscope in which the hardness adjustment mechanism operates smoothly.

DESCRIPTION OF EMBODIMENTS

First Embodiment

Figure 1:
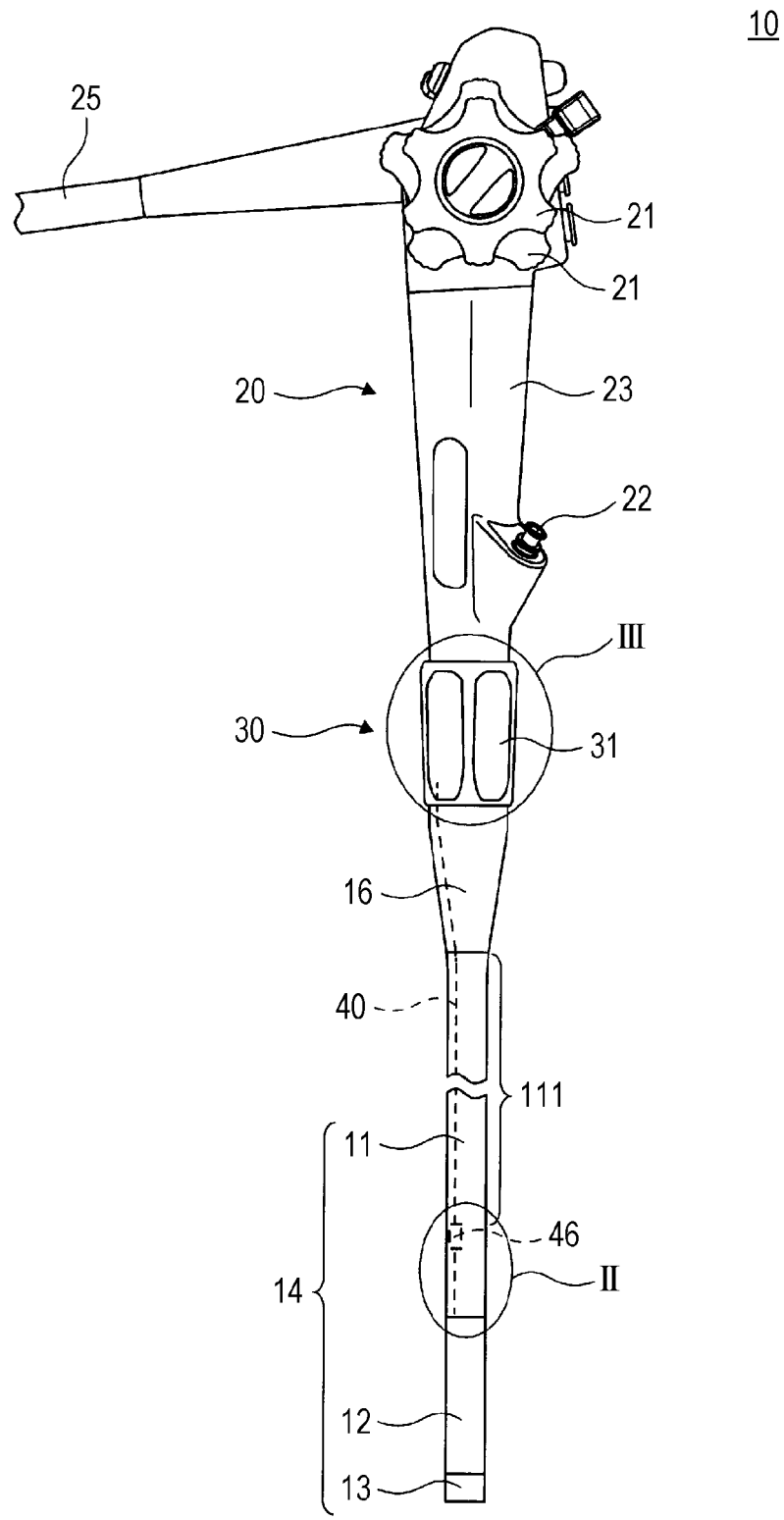
FIG. 1 is an exterior view of an endoscope.

FIG. 1 is an exterior view of an endoscope 10. The endoscope 10 of the present embodiment is a colonoscope. The endoscope 10 includes an insertion portion 14, a hardness adjustment operation unit 30, an operation unit 20, and a universal cord 25. The operation unit 20 includes a bending knob 21 and a channel inlet 22. The surface of the hardness adjustment operation unit 30 is covered with a hardness adjustment knob 31.

The endoscope 10 of the present embodiment has a so-called hardness adjustment function that enables a doctor who is a user to adjust the hardness of a soft portion 11 by operating the hardness adjustment knob 31 during an endoscopic examination. More specifically, the user can adjust the hardness of a hardness changing portion 111 which is a part of the soft portion 11. Here, the hardness of the soft portion 11 means the flexural rigidity of the soft portion 11. In the following description, a high hardness of the soft portion 11 means a high flexural rigidity of the soft portion 11, and a low hardness of the soft portion 11 means a low flexural rigidity of the soft portion 11.

The insertion portion 14 is long and has one end connected to the operation unit 20 via a bend preventing portion 16. The insertion portion 14 includes the soft portion 11, a bending section 12, and a distal tip 13 in this order from the operation unit 20 side. The bending section 12 is bent according to an operation of the bending knob 21.

A hardness adjustment cable 40 is arranged between the hardness adjustment operation unit 30 and a boundary portion between the soft portion 11 and the bending section 12. A configuration of the hardness adjustment cable 40 will be described later. From the channel inlet 22 to the distal tip 13, a channel penetrating the insertion portion 14 is provided.

In the following description, a longitudinal direction of the insertion portion 14 is referred to as an insertion direction. Similarly, a side close to the operation unit 20 along the insertion direction is referred to as an operation unit side, and a side distant from the operation unit 20 is referred to as a distal tip side.

The universal cord 25 is long, and has a first end connected to the operation unit 20 and a second end connected to a connector unit (not illustrated). The connector unit is connected to a processor for an endoscope and the like (not illustrated).

Figure 2:
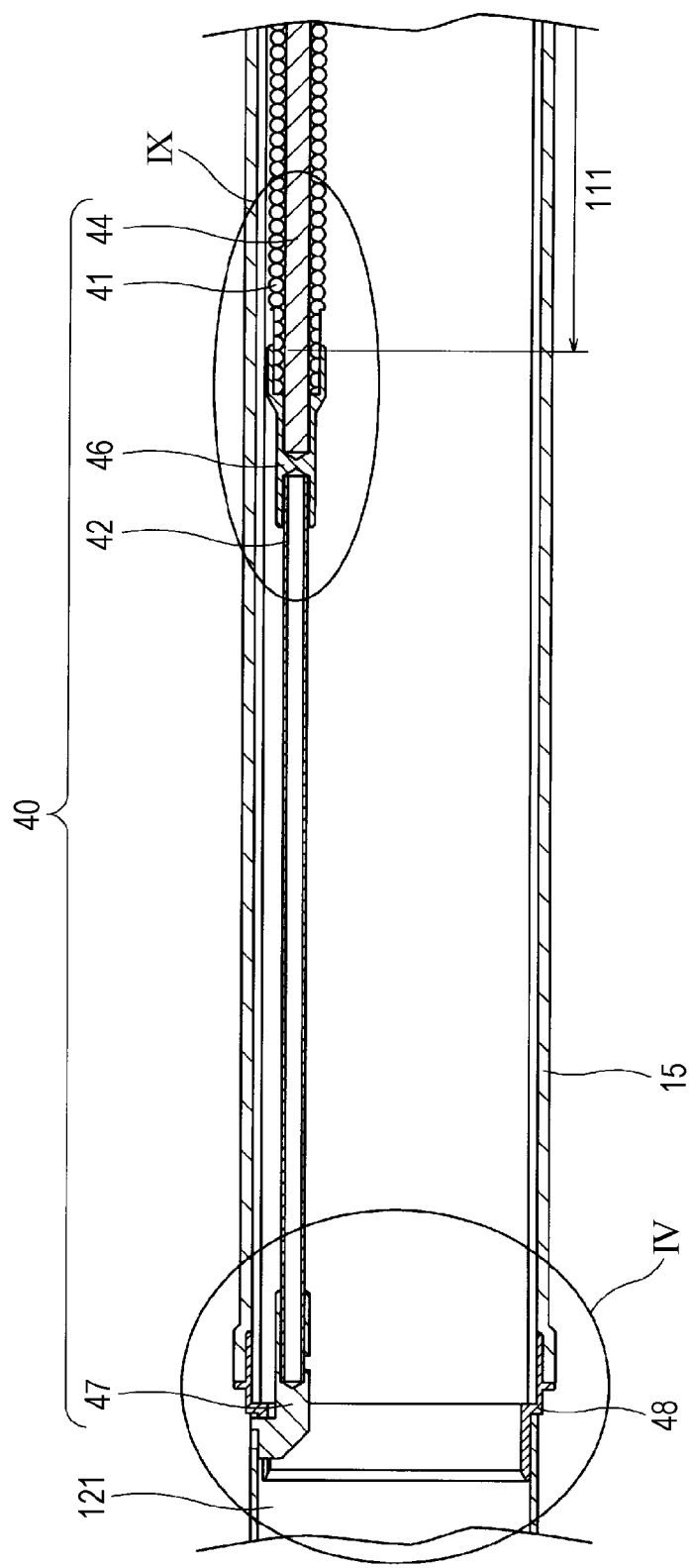
FIG. 2 is a cross-sectional view of Part II in FIG. 1.

FIG. 2 is a cross-sectional view of Part II in FIG. 1. In each cross-sectional view including FIG. 2, built-in objects other than a hardness adjustment mechanism, such as a cable, an air supply tube, a water supply tube, the channel, a bending wire, and the like are not illustrated.

FIG. 2 illustrates a distal tip portion of the soft portion 11. The surface of the soft portion 11 is covered with an exterior tube 15. A plurality of tubular bending pieces 121 are arranged in the bending section 12. FIG. 2 illustrates a part of the bending piece 121 arranged closest to the operation unit. A bending rubber covering the bending piece 121 is not illustrated. The exterior tube 15 and the bending piece 121 are connected by a connecting pipe 48.

The hardness adjustment cable 40 has a hardness adjustment sheath 41, a hardness adjustment wire 44, a coupling tool 46, a connecting cable 42, and a distal tip locking tool 47. The connecting cable 42 is arranged on the distal tip side of the insertion portion 14, and the hardness adjustment sheath 41 and the hardness adjustment wire 44 are arranged on the operation unit side of the insertion portion 14. The hardness adjustment wire 44 is inserted through the hardness adjustment sheath 41. The connecting cable 42, the hardness adjustment sheath 41, and the hardness adjustment wire 44 are coupled by the coupling tool 46.

The hardness adjustment sheath 41 is configured using a tightly wound coil in which a round strand is tightly wound. The connecting cable 42 is configured using a tightly wound coil in which a flat strand is tightly wound. A tensile rigidity of the connecting cable 42 is lower than a tensile rigidity of the hardness adjustment sheath 41. The hardness adjustment sheath may be configured using a resin tube. The connecting cable 42 may be configured using a wire. Details of the coupling tool 46 and the distal tip locking tool 47 will be described later.

Figure 3:
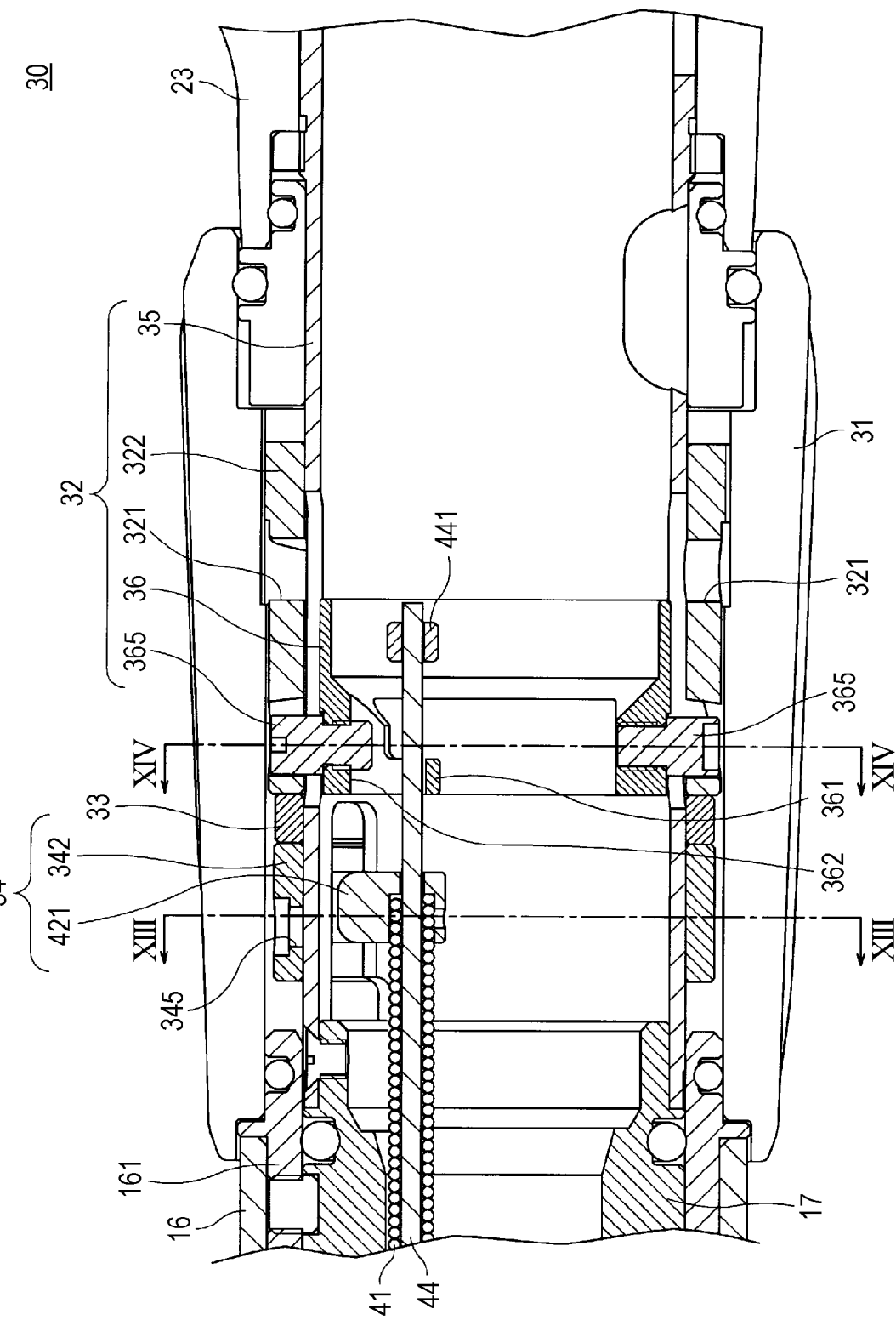
FIG. 3 is a cross-sectional view of Part III in FIG. 1.

FIG. 3 is a cross-sectional view of Part III in FIG. 1. FIG. 3 illustrates a state in which the hardness of the soft portion 11 is set to the lowest state and the entire insertion portion 14 is substantially straight. A guide frame 35 is inserted through the hardness adjustment knob 31. The guide frame 35 has a substantially cylindrical shape. The guide frame 35 has a central axis in a direction that coincides with the longitudinal direction of the insertion portion 14.

On the right side of FIG. 3, an operation unit housing 23 is fixed to the outer side of the guide frame 35. The operation unit housing 23 is a housing that constitutes the operation unit 20. On the left side of FIG. 3, a rear end cap 17 attached to an end portion of the insertion portion 14 is fixed to the inner side of the guide frame 35. The rear end cap 17 is covered with the bend preventing portion 16. A bend preventing cap 161 is fixed to an end portion of the bend preventing portion 16 on the operation unit side. The operation unit 20 and the insertion portion 14 are fixed to each other so as not to rotate via the guide frame 35.

A cam ring 322, a collar ring 33, and a sheath fixing ring 342 are arranged in this order from the operation unit 20 side between the guide frame 35 and the hardness adjustment knob 31. The cam ring 322, the collar ring 33, and the sheath fixing ring 342 are independently movable in the longitudinal direction of the guide frame 35.

The cam ring 322 is coupled to the hardness adjustment knob 31. When the user turns the hardness adjustment knob 31, the cam ring 322 rotates integrally with the hardness adjustment knob 31. The cam ring 322 is one of components of a cam mechanism 32 to be described later. Configurations of the cam ring 322 and the cam mechanism 32 will be described later.

The collar ring 33 has a cylindrical shape having an inner diameter larger than an outer diameter of the guide frame 35 and an outer diameter smaller than an inner diameter of the hardness adjustment knob 31. The collar ring 33 can freely move in an axial direction of the guide frame 35 between the cam ring 322 and the sheath fixing ring 342.

The collar ring 33 is made of a highly lubricious resin, for example, polyacetal, polytetrafluoroethylene, hard polyethylene, or the like. The collar ring 33 may be made of metal that has been subjected to surface treatment for enhancing lubricity, for example, fluororesin coating, hard chrome plating, or the like.

A sheath receiver 421 is fixed to an end portion of the hardness adjustment sheath 41 on the operation unit side so as not to interfere with an operation of the hardness adjustment wire 44 in the longitudinal direction. The sheath receiver 421 is fixed to the sheath fixing ring 342 by two fixing screws 341 (see FIG. 11). The sheath fixing ring 342 and the sheath receiver 421 are components of a sheath fixing unit 34. A configuration of the sheath fixing unit 34 will be described later.

A driven body 36 having a substantially cylindrical shape is arranged inside the guide frame 35. The driven body 36 has a substantially cylindrical shape coaxial with the guide frame 35. An outer diameter of the driven body 36 is slightly smaller than an inner diameter of the guide frame 35. The driven body 36 has a wire holding portion 361 protruding inward.

The wire holding portion 361 is provided with a wire hole 362 penetrating along an axial direction of the driven body 36. The hardness adjustment wire 44 protruding from the end portion of the hardness adjustment sheath 41 on the operation unit side penetrates the wire hole 362. A retaining member 441 is fixed to an end portion of the hardness adjustment wire 44.

Figure 4:
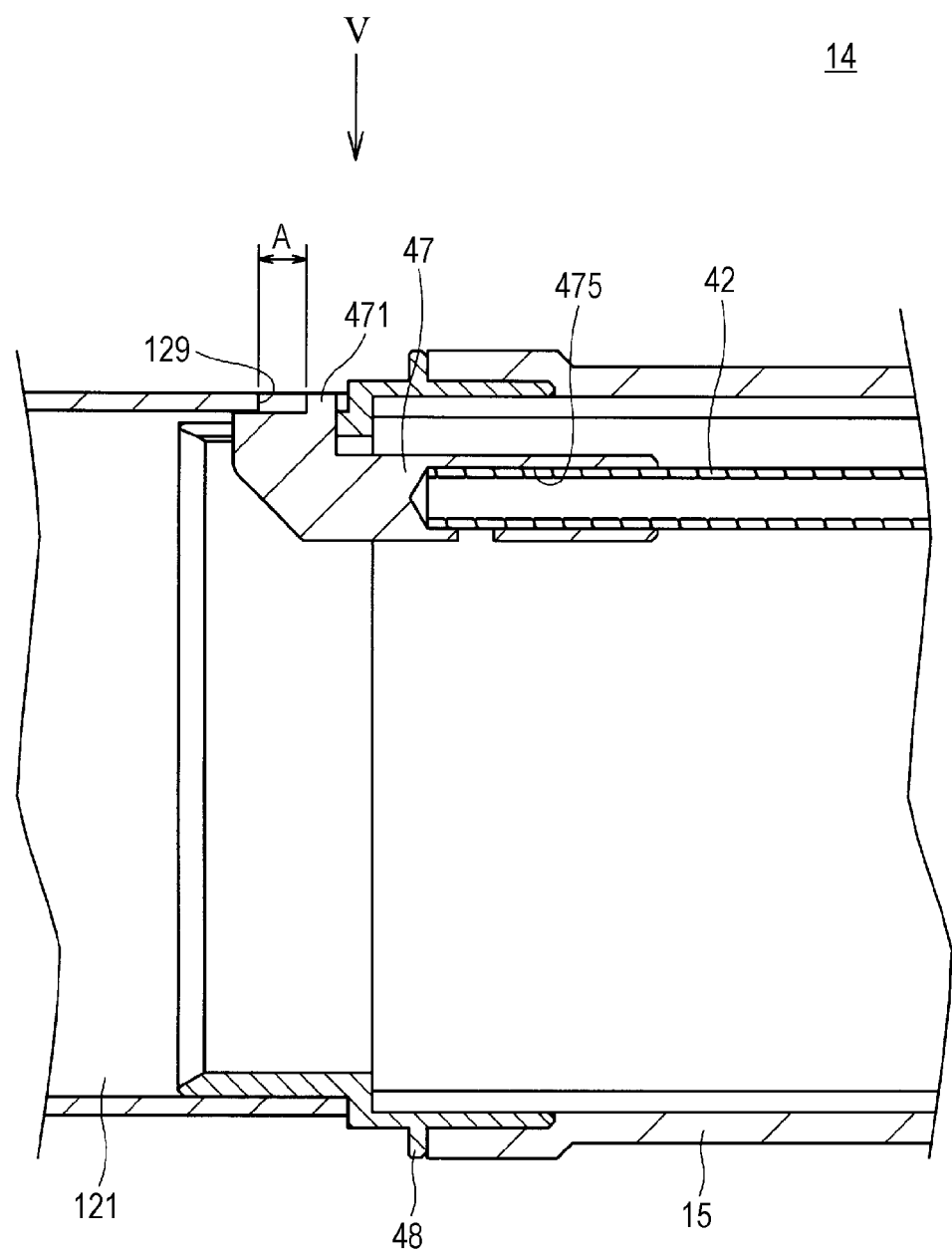
FIG. 4 is an enlarged view of Part IV in FIG. 2.
Figure 5:
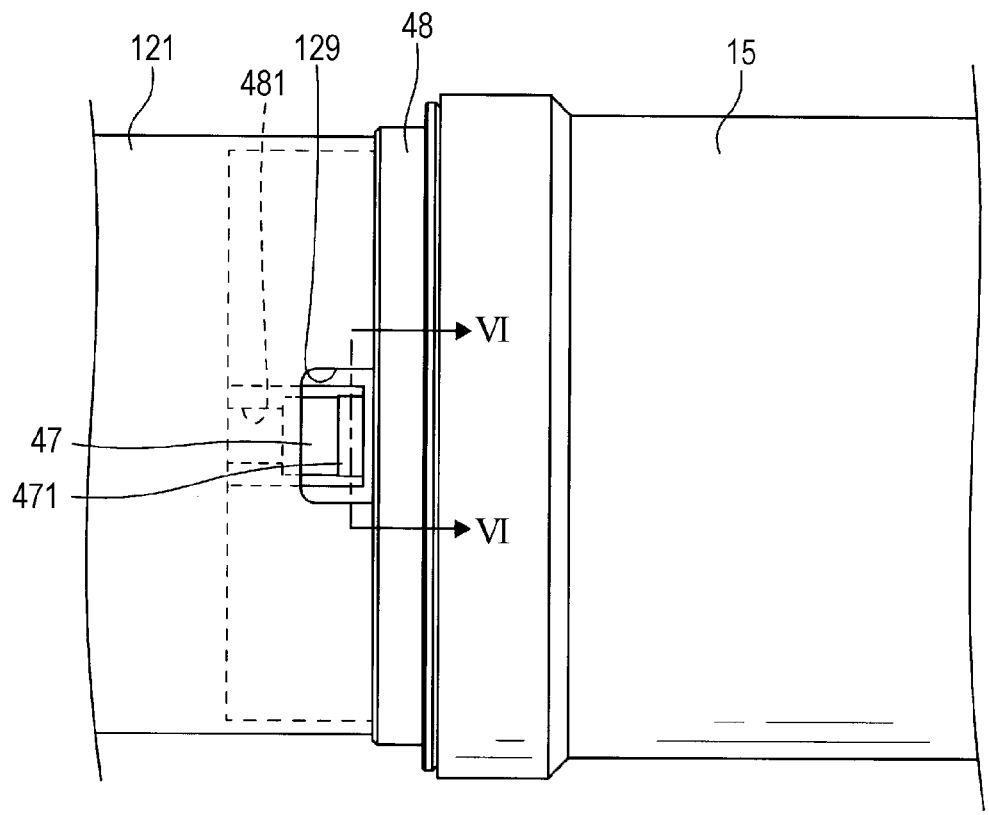
FIG. 5 is a view seen from a direction of an arrow V in FIG. 4.
Figure 6:
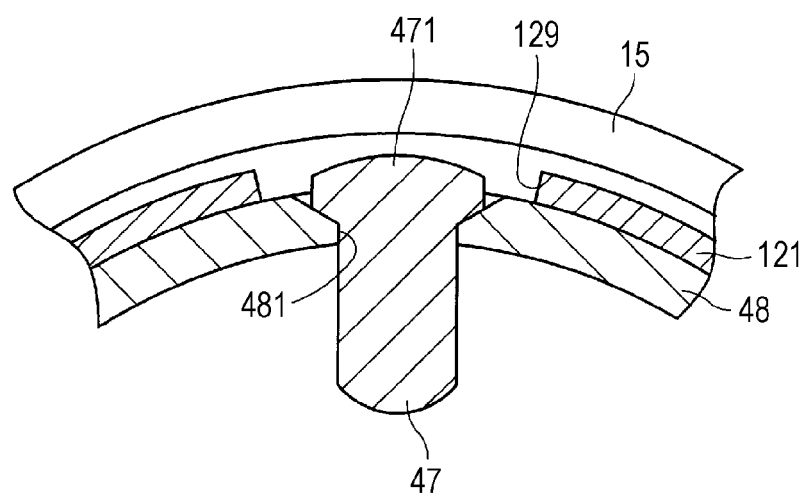
FIG. 6 is a partial cross-sectional view of an insertion portion taken along line VI-VI in FIG. 5.
Figure 7:
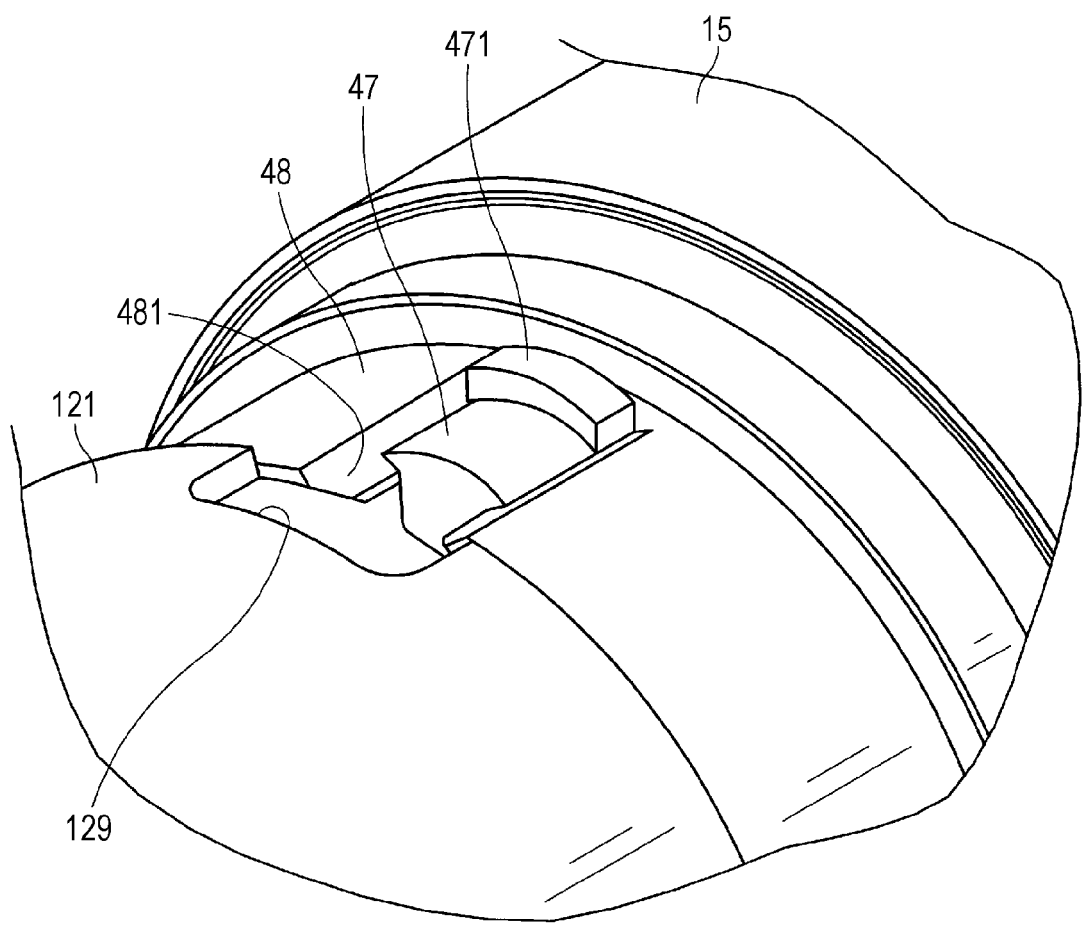
FIG. 7 is an exploded perspective view of the insertion portion.
Figure 8:
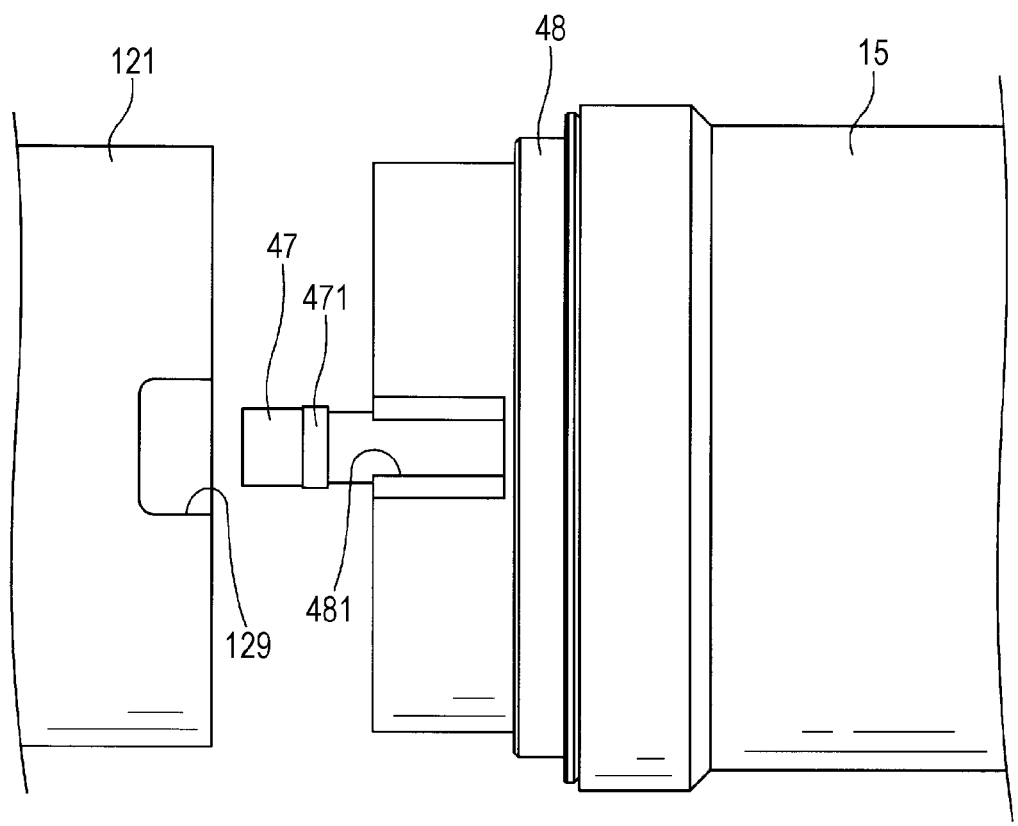
FIG. 8 is an exploded view of the insertion portion.

FIG. 4 is an enlarged view of Part IV in FIG. 2. FIG. 5 is a view seen from a direction of an arrow V in FIG. 4. FIG. 6 is a partial cross-sectional view of the insertion portion 14 taken along line VI-VI in FIG. 5. FIG. 7 is an exploded perspective view of the insertion portion 14. FIG. 7 illustrates a state in which the bending piece 121 is slid to the distal tip side. FIG. 8 is an exploded view of the insertion portion 14. FIG. 8 illustrates a state in which each of the bending piece 121 and the distal tip locking tool 47 is slid to the distal tip side. A configuration of the distal tip portion of the soft portion 11 will be described with reference to FIGS. 4 to 8.

The distal tip locking tool 47 is fixed to an end portion of the connecting cable 42. The distal tip locking tool 47 has a substantially L-shape with one end facing the operation unit side and the other end facing the outer side of the insertion portion 14. The distal tip locking tool 47 has a fixing hole 475 at an end portion facing the operation unit side. The end portion of the connecting cable 42 is fixed inside the fixing hole 475 by any technique such as adhesion and brazing. A locking protrusion 471 is provided at an end on the operation unit side of an end surface of the distal tip locking tool 47 facing the outer side of the insertion portion 14.

As illustrated in FIGS. 5, 7 and 8, a locking tool groove 481 that is open to the distal tip side is provided on a side surface of the connecting pipe 48. A receiving groove 129 that is open to the operation unit side is provided at a position corresponding to the locking tool groove 481 on a side surface of the bending piece 121. The locking protrusion 471 is arranged in a distal tip holding portion formed by a portion where the locking tool groove 481 and the receiving groove 129 overlap.

As illustrated in FIGS. 6 and 7, a cross-sectional shape of the locking tool groove 481 is a substantially V-shaped groove shape having a wide width on the outer peripheral side. A cross-sectional shape of the distal tip locking tool 47 is also wide on the outer peripheral side of the insertion portion 14. As illustrated in FIG. 6, a distal tip portion of the distal tip locking tool 47 is covered with an edge of the receiving groove 129.

With the above configuration, the distal tip locking tool 47 can move in the longitudinal direction within a range of a length A illustrated in FIG. 4. The distal tip locking tool 47 is held by the locking tool groove 481 and the bending piece 121, and thus, does not move in a radial direction of the insertion portion 14.

Figure 9:
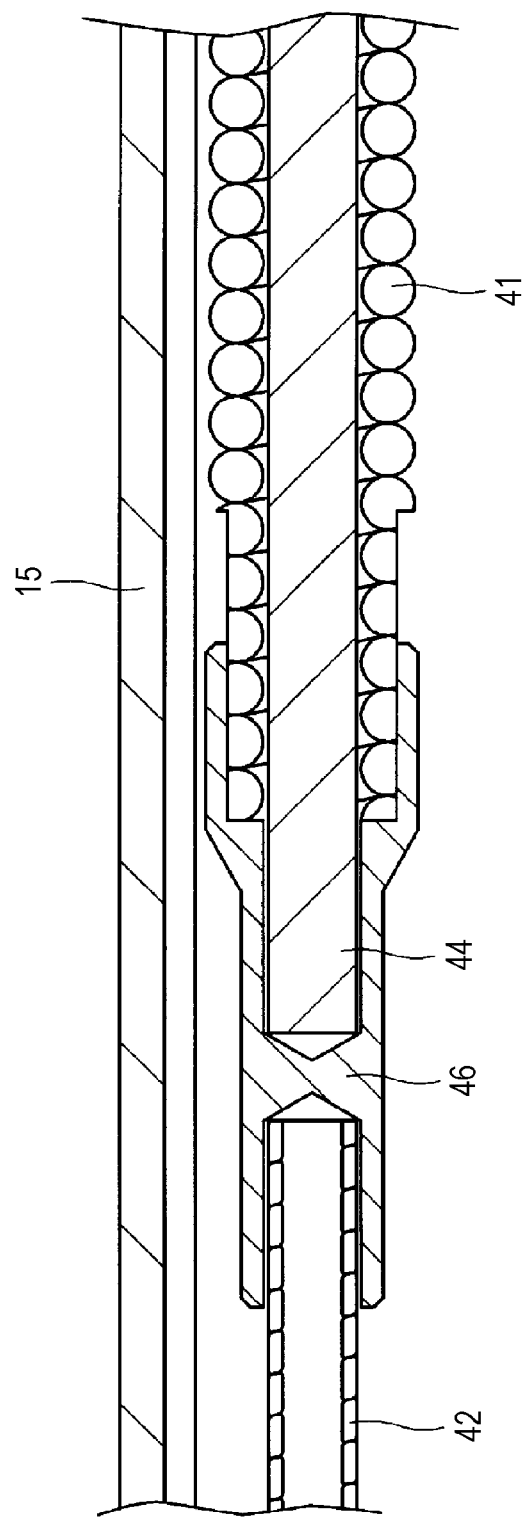
FIG. 9 is an enlarged view of Part IX in FIG. 2.

FIG. 9 is an enlarged view of Part IX in FIG. 2. The coupling tool 46 has a stepped cylindrical shape that is thicker on the operation unit side than on the distal tip side. Both end surfaces of the coupling tool 46 have respective holes. The end portion of the connecting cable 42 is fixed inside the hole on the distal tip side by any technique such as adhesion and brazing.

The hole on the operation unit side of the coupling tool 46 is a stepped hole. The hardness adjustment wire 44 is fixed to a small diameter portion on the inner side by any technique such as adhesion and brazing. The hardness adjustment sheath 41 abuts against a stepped portion of the stepped hole. The hardness adjustment sheath 41 is fixed to a large diameter portion of the stepped hole by any means such as adhesion and brazing.

The outer circumference of the end portion of the hardness adjustment sheath 41 has been removed to reduce the diameter. As a result, fixing strength is increased by increasing the contact area between the hardness adjustment sheath 41 and the coupling tool 46, and the diameter of the insertion portion 14 is reduced.

Since the holes provided at both the ends of the coupling tool 46 do not communicate with each other, the connecting cable 42 and the hardness adjustment wire 44 can abut against and be fixed to bottoms of the respective holes. Therefore, it is unnecessary to manage each insertion length of the connecting cable 42 and the hardness adjustment wire 44 into the coupling tool 46 at the time of assembly, and the assembly is easy.

In addition, it is possible to prevent trouble that an adhesive used to fix the connecting cable 42, for example, closes the hole on the hardness adjustment wire 44 side to hinder assembling of the hardness adjustment wire 44 since the holes provided at both the ends of the coupling tool 46 do not communicate with each other. The holes provided at both the ends of the coupling tool 46 may communicate with each other through, for example, a small hole at the center. In such a case, process management is performed such that trouble such as outflow of adhesive does not occur.

Figure 10:
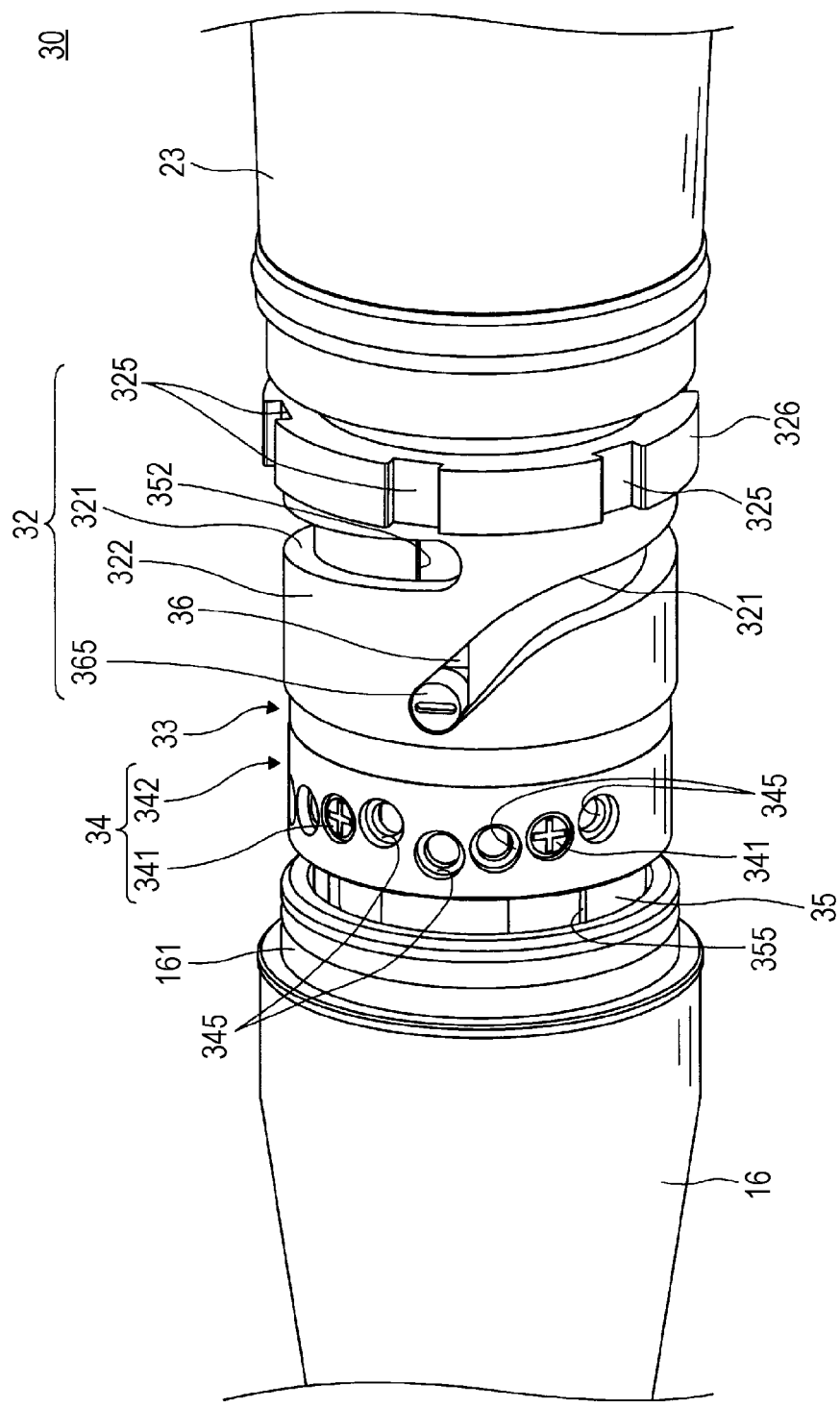
FIG. 10 is a perspective view of a hardness adjustment operation unit from which a hardness adjustment knob has been removed.
Figure 11:
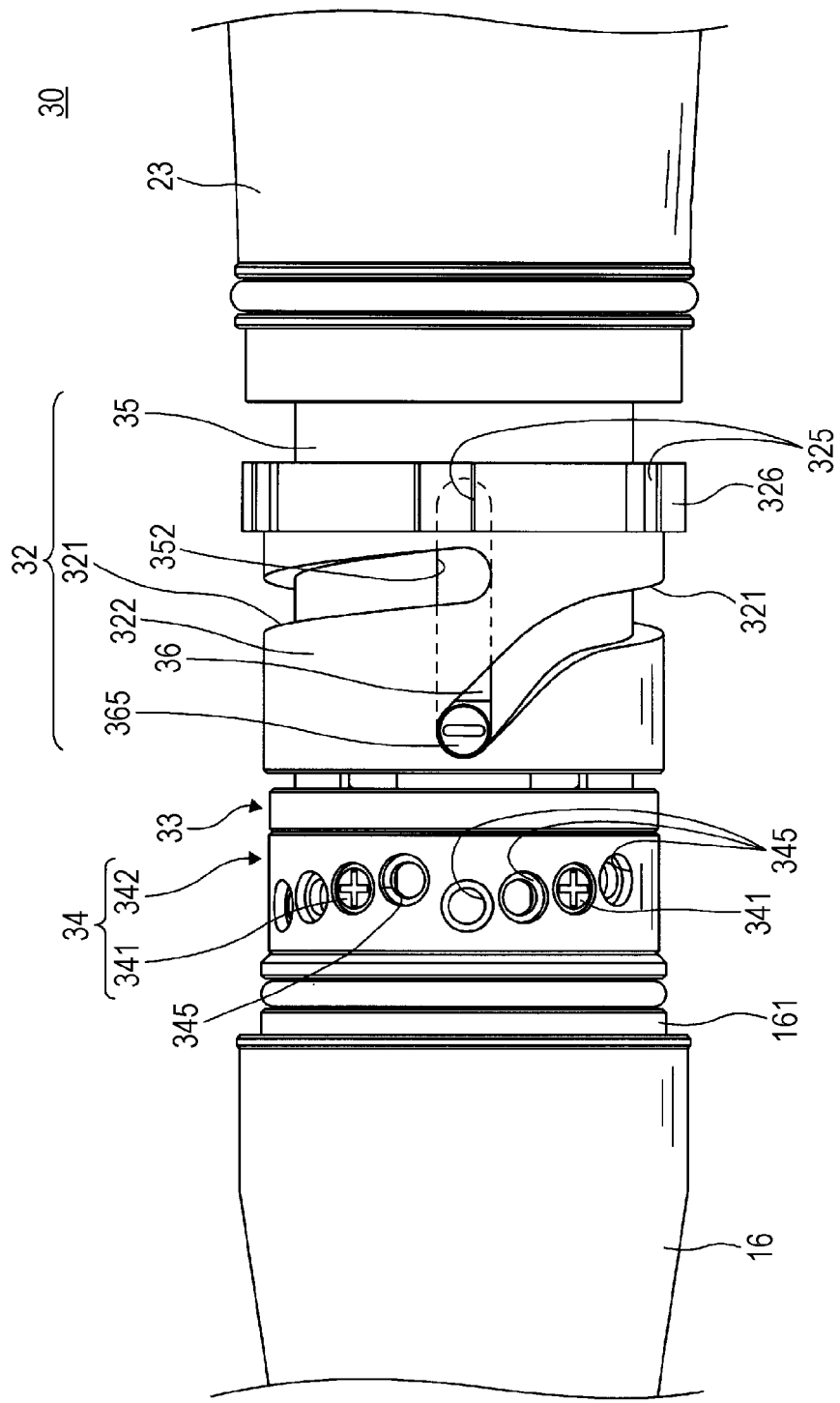
FIG. 11 is a front view of the hardness adjustment operation unit from which the hardness adjustment knob has been removed.

FIG. 10 is a perspective view of the hardness adjustment operation unit 30 from which the hardness adjustment knob 31 has been removed. FIG. 10 illustrates a state in which the hardness of the soft portion 11 is set to the lowest state as in FIG. 3 and the entire insertion portion 14 is substantially straight. FIG. 11 is a front view of the hardness adjustment operation unit 30 from which the hardness adjustment knob 31 has been removed. FIG. 11 illustrates a state in which the sheath fixing ring 342 is slid to the distal tip side. The slide of the sheath fixing ring 342 will be described later.

Figure 12:
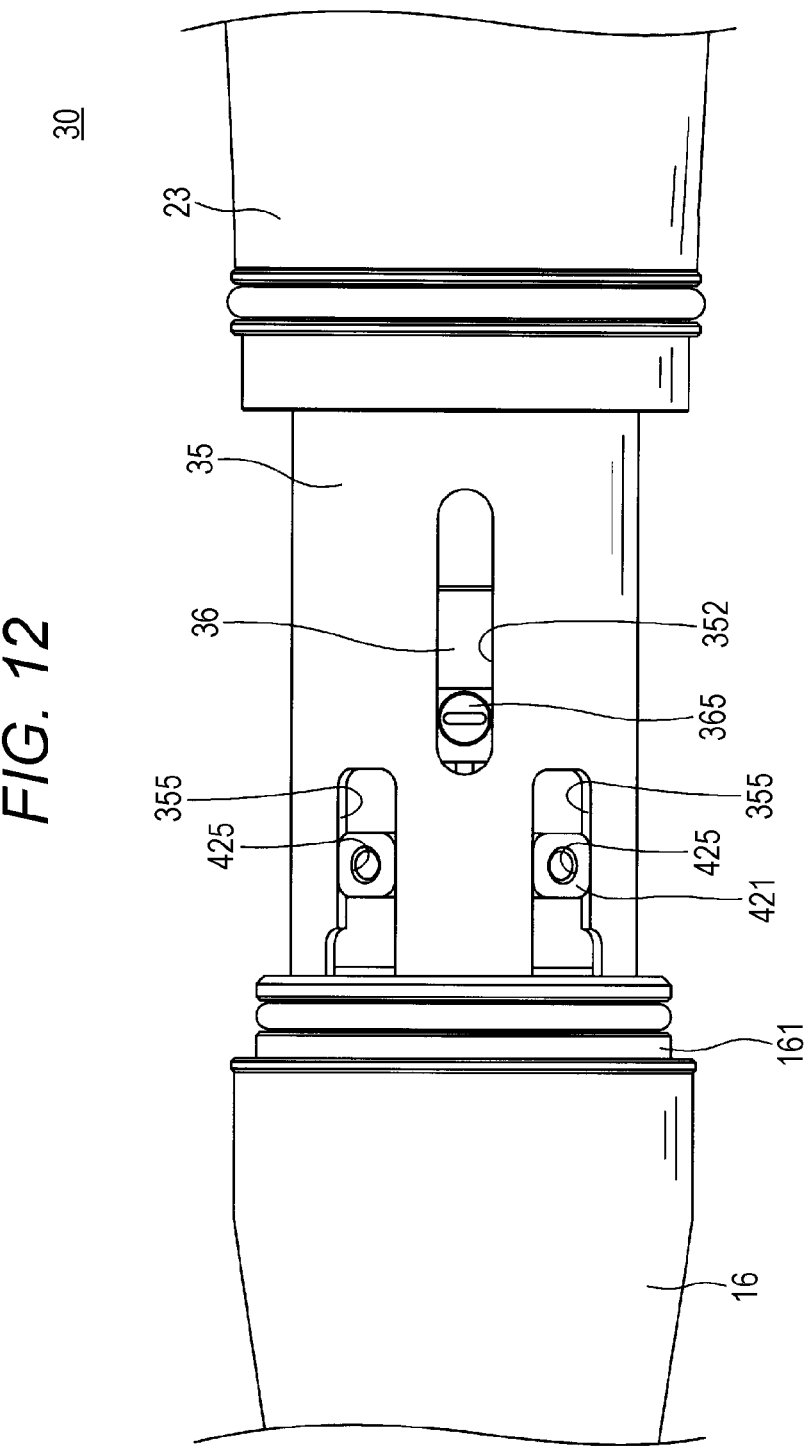
FIG. 12 is a front view of the hardness adjustment operation unit from which the hardness adjustment knob, a cam ring, and collar and sheath fixing rings have been removed.
Figure 13:
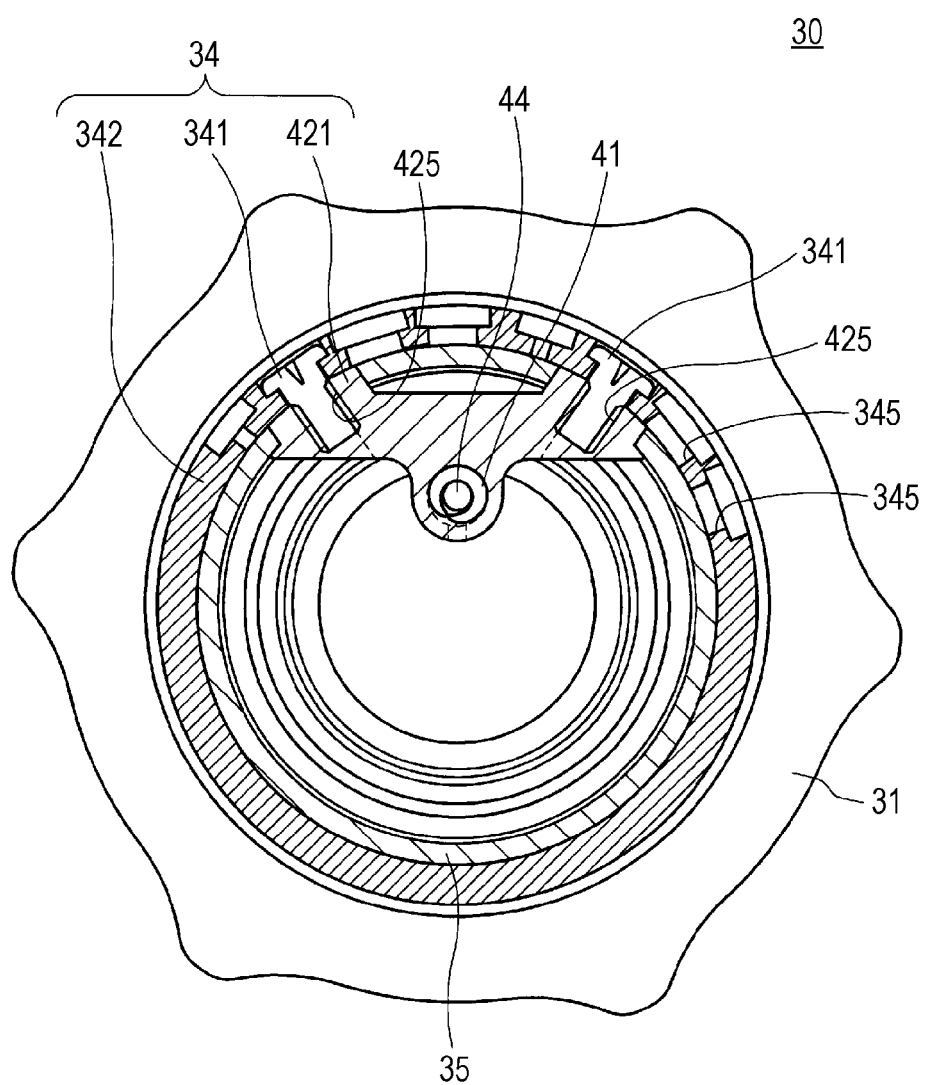
FIG. 13 is a partial cross-sectional view of the hardness adjustment operation unit taken along line XIII-XIII in FIG. 3.
Figure 14:
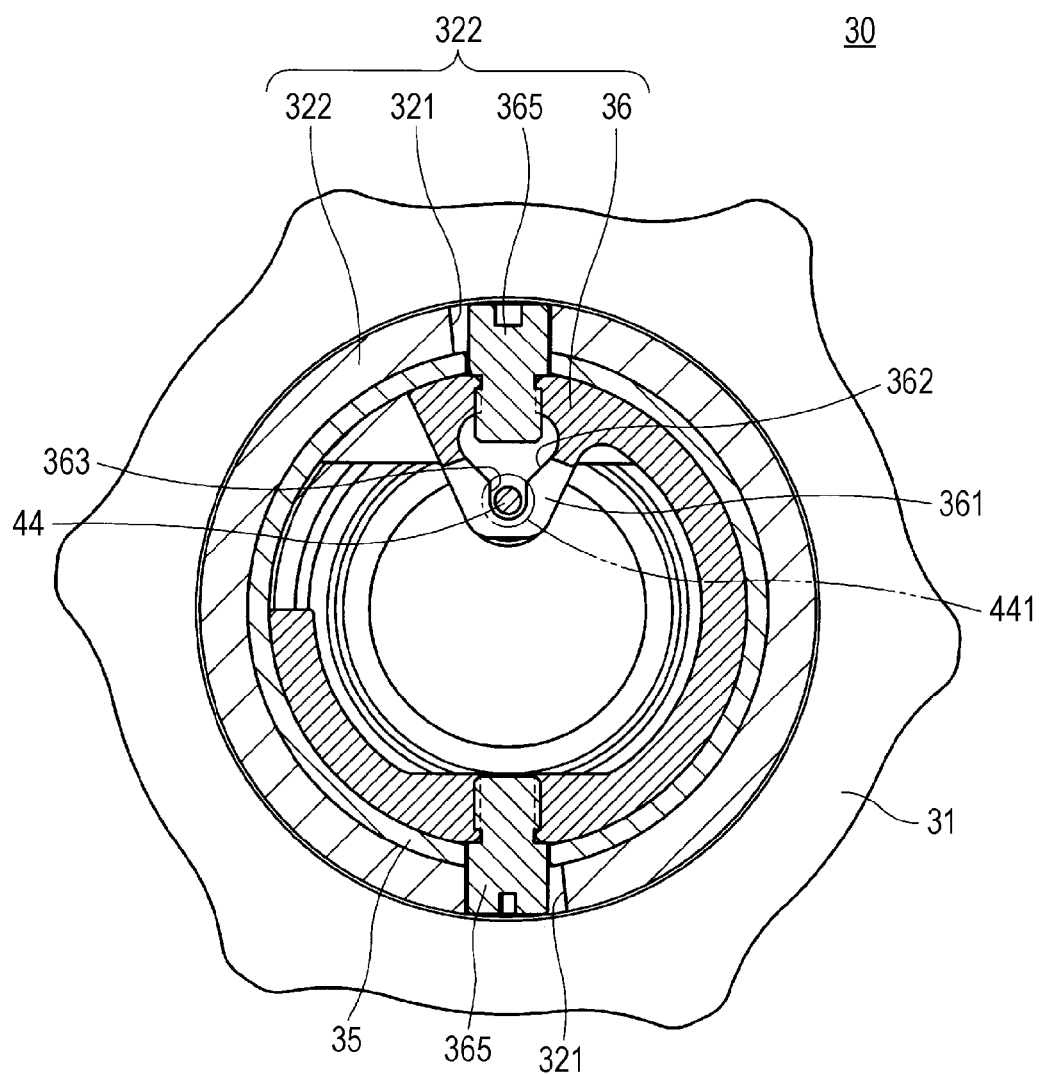
FIG. 14 is a partial cross-sectional view of the hardness adjustment operation unit taken along line XIV-XIV in FIG. 3.

FIG. 12 is a front view of the hardness adjustment operation unit 30 from which the hardness adjustment knob 31, the cam ring 322, the collar ring 33, and the sheath fixing ring 342 have been removed. FIG. 12 illustrates a state in which the hardness of the soft portion 11 is set to the lowest state as in FIG. 3 and the entire insertion portion 14 is substantially straight. FIG. 13 is a partial cross-sectional view of the hardness adjustment operation unit 30 taken along line XIII-XIII in FIG. 3. FIG. 14 is a partial cross-sectional view of the hardness adjustment operation unit 30 taken along line XIV-XIV in FIG. 3.

As illustrated in FIGS. 10 and 11, the cam ring 322 has a stepped cylindrical shape that has a knob engagement portion 326 having a large diameter on the operation unit side. The knob engagement portion 326 is provided with a plurality of knob engagement grooves 325 extending in the longitudinal direction. As the knob engagement groove 325 engages with a protrusion (not illustrated) provided on an inner surface of the hardness adjustment knob 31, the cam ring 322 rotates in conjunction with the rotation of the hardness adjustment knob 31.

Two first cam grooves 321 are provided on a side surface of the cam ring 322. The two first cam grooves 321 have the same shape and are arranged to be axially symmetrical about a central axis of the cam ring 322. The first cam groove 321 is inclined with respect to an end surface of the cam ring 322 on the distal tip side, and is substantially parallel to an end surface of the cam ring 322 on the operation unit side.

The sheath fixing ring 342 has adjustment holes 345 each having a deep countersunk shape on a side surface. Two adjustment holes 345 having the same distance from the end surface form one set, and a total of four sets of the adjustment holes 345 are arranged. The distances between the adjustment holes 345 forming the respective sets are equal. Note that the number of the adjustment holes 345 is not limited to eight pieces in four sets. Any number of the adjustment holes 345 can be arranged.

As illustrated in FIG. 12, second cam grooves 352 are provided on the operation unit side of a side surface of the guide frame 35. Two second cam grooves 352 are arranged to be axially symmetrical about a central axis of the guide frame 35. The guide frame 35 is provided with two slide grooves 355 on the side surface on the distal tip side.

As illustrated in FIGS. 3 and 14, the driven body 36 is arranged on the inner side of the guide frame 35. The driven body 36 has a C-ring shape and has the wire holding portion 361 that protrudes inward from one edge of the C-ring. The wire holding portion 361 is provided on the distal tip side of the driven body 36. The wire holding portion 361 is provided with the wire hole 362 penetrating along the axial direction of the guide frame 35.

A wire slit 363 having a width that allows passage of the hardness adjustment wire 44 and does not allow passage of the retaining member 441 is provided on an edge of the wire hole 362. In FIG. 14, the retaining member 441 is illustrated by an imaginary line. Note that the wire hole 362 has a dimension that allows the retaining member 441 to easily pass through when a cam pin 365 is not screwed or is screwed shallowly. In a state in which the cam pin 365 is screwed, the retaining member 441 is not able to pass through the wire hole 362. Therefore, the retaining member 441 does not move to the distal tip side of the driven body 36.

The driven body 36 is provided with two screw holes penetrating a side surface symmetrically with respect to a central axis. One of the screw holes penetrates toward the wire hole 362. The cam pin 365 is screwed into each of the two screw holes. A head of the cam pin 365 passes through the second cam groove 352 and the first cam groove 321. An end surface of the head of the cam pin 365 is arranged on the inner side of the side surface of the cam ring 322.

When the cam ring 322 rotates, the driven body 36 moves in the central-axis direction by action of the first cam groove 321, the second cam groove 352, and the cam pin 365. That is, the cam ring 322 in which the first cam groove 321 is formed, the guide frame 35 in which the second cam groove 352 is formed, and the driven body 36 in which the cam pin 365 is fixed constitute the cam mechanism 32 that converts rotational movement about the central axis into forward and backward movement along the central axis.

As illustrated in FIG. 13, the sheath receiver 421 is a substantially Y-shaped plate. As illustrated in FIG. 3, a stepped hole that is thick on the distal tip side and thin on the operation unit side is provided in a portion corresponding to a vertical line on the lower side of the Y-shape. The end portion of the hardness adjustment sheath 41 is fixed to a large diameter portion of the stepped hole by any technique such as adhesion and brazing. A small diameter portion of the stepped hole is thicker than an outer diameter of the hardness adjustment wire 44, and the hardness adjustment wire 44 can smoothly move forward and backward.

As illustrated in FIGS. 12 and 13, a portion corresponding to two diagonal lines on the upper side of the Y-shape is engaged with the slide groove 355 from the inner side of the guide frame 35. The sheath receiver 421 is provided with fixing screw holes 425 respectively on two end surfaces corresponding to the upper side of the Y-shape. One set of the four sets of adjustment holes 345 described above and the fixing screw holes 425 are combined by the two fixing screws 341. The sheath receiver 421, the sheath fixing ring 342, and the fixing screw 341 constitute the sheath fixing unit 34 that moves forward and backward integrally with the end portion of the hardness adjustment sheath 41 on the operation unit side.

As illustrated in FIG. 13, the hardness adjustment knob 31 has a substantially hexagonal cross section. A center portion of each side is recessed. Therefore, the user can surely rotate the hardness adjustment knob 31 without slipping even in the state of wearing medical gloves.

Figure 15:
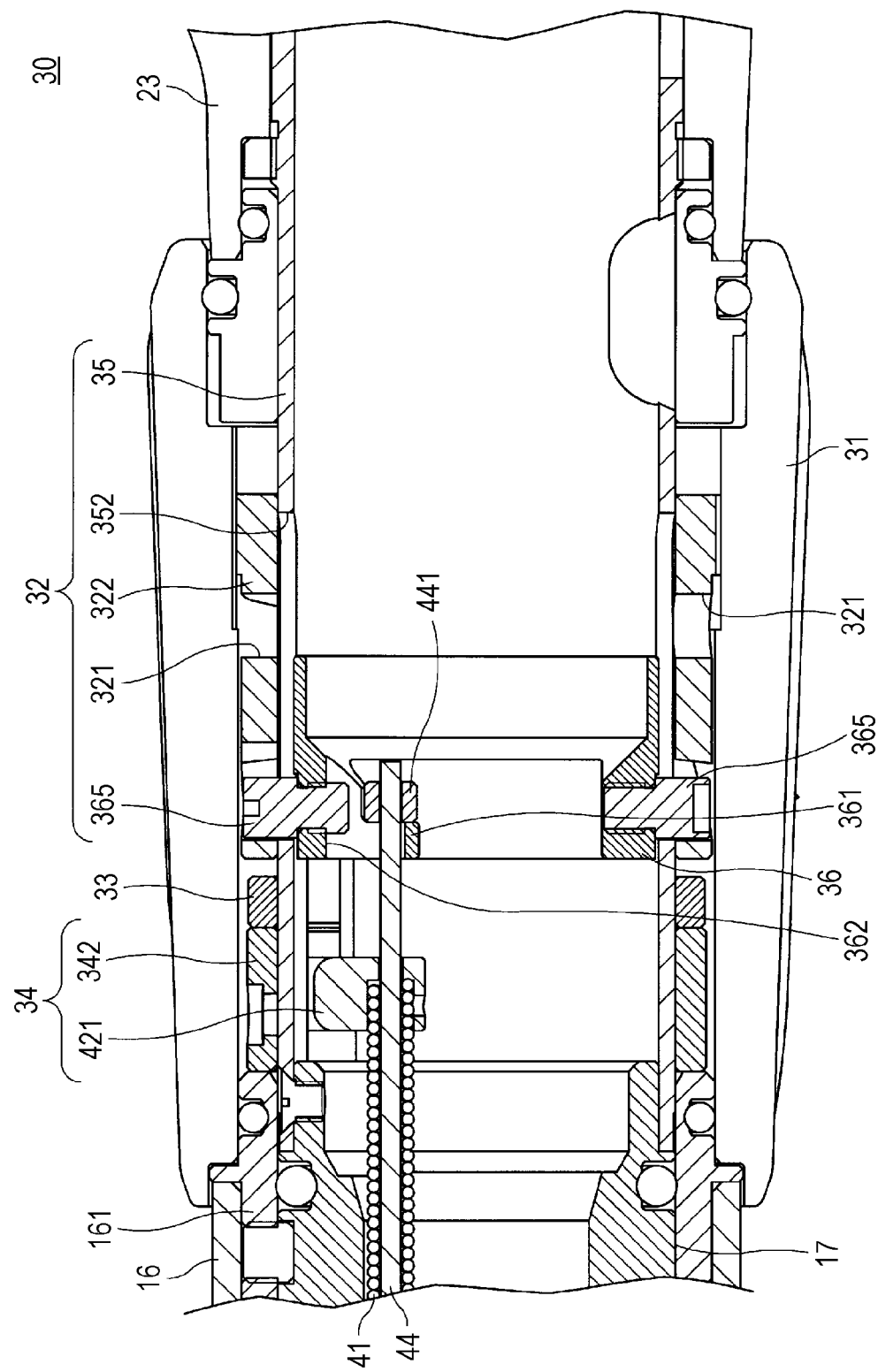
FIG. 15 is a cross-sectional view of the hardness adjustment operation unit when a hardness adjustment cable is pulled into a distal tip side.

FIG. 15 is a cross-sectional view of the hardness adjustment operation unit 30 when the hardness adjustment cable 40 is pulled into the distal tip side. The slide of the sheath fixing ring 342 will be described with reference to FIGS. 3, 10, 11 and 15.

The user starts inserting the insertion portion 14 into large intestine in a state in which the hardness of the soft portion 11 is low. The hardness adjustment operation unit 30 at the time of starting the insertion is in the state described with reference to FIGS. 3 and 10. The user inserts the insertion portion 14 into the large intestine while appropriately operating the bending knob 21. As the insertion progresses, the hardness adjustment cable 40 is pulled into the distal tip side due to the bending of the bending section 12 and a flexure of the soft portion 11. In the following description, the bending of the bending section 12 and the flexure of the soft portion 11 will be sometimes collectively referred to as a flexure of the insertion portion 14.

As a result that the hardness adjustment sheath 41 is pulled into the distal tip side, the sheath fixing unit 34 slides to the distal tip side as illustrated in FIGS. 11 and 15. As a result that the hardness adjustment wire 44 is pulled into the distal tip side, the retaining member 441 slides to the distal tip side as illustrated in FIG. 15.

An operation of the distal tip locking tool 47 will be described with reference to FIGS. 2, 4, 11 and 15. As illustrated in FIGS. 11 and 15, a rear end side of the hardness adjustment sheath 41 is no longer pulled into the insertion portion 14 when the sheath fixing ring 342 abuts against the bend preventing cap 161. Similarly, a rear end side of the hardness adjustment wire 44 is no longer pulled into the insertion portion 14 when the retaining member 441 abuts against the driven body 36.

When the hardness adjustment cable 40 is pulled into the insertion portion 14 with the rear end side fixed in this manner, the coupling tool 46 is pushed out to the distal tip side. As the distal tip locking tool 47 slides within the range of the length A illustrated in FIG. 4, a compressive force applied to the hardness adjustment cable 40 is reduced.

A slide mechanism of the sheath fixing ring 342, a slide mechanism of the distal tip locking tool 47, and a slide mechanism of the retaining member 441 described above reduce the tension and compressive force applied to the hardness adjustment cable 40 due to the flexure of the insertion portion 14. Therefore, it is possible to provide the endoscope 10 in which the hardness of the soft portion 11 hardly varies even when the insertion portion 14 is flexural.

As illustrated in FIG. 11, the fixing screw 341 is attached using the adjustment hole 345 such that there is a gap that allows the collar ring 33 to move in the axial direction in a state in which the cam pin 365 is located at an end of the first cam groove 321 on the distal tip side. Since the sheath fixing ring 342 is provided with the plurality of sets of adjustment holes 345, the sheath fixing ring 342 can be fixed in an appropriate position even if the length of the exterior tube 15 and the length of the hardness adjustment sheath 41 vary.

An operation of the hardness adjustment mechanism will be described. When it is necessary to increase the hardness of the soft portion 11, the user rotates the hardness adjustment knob 31 clockwise as viewed from the operation unit side. As described above, the cam ring 322 rotates in conjunction with the hardness adjustment knob 31.

Figure 16:
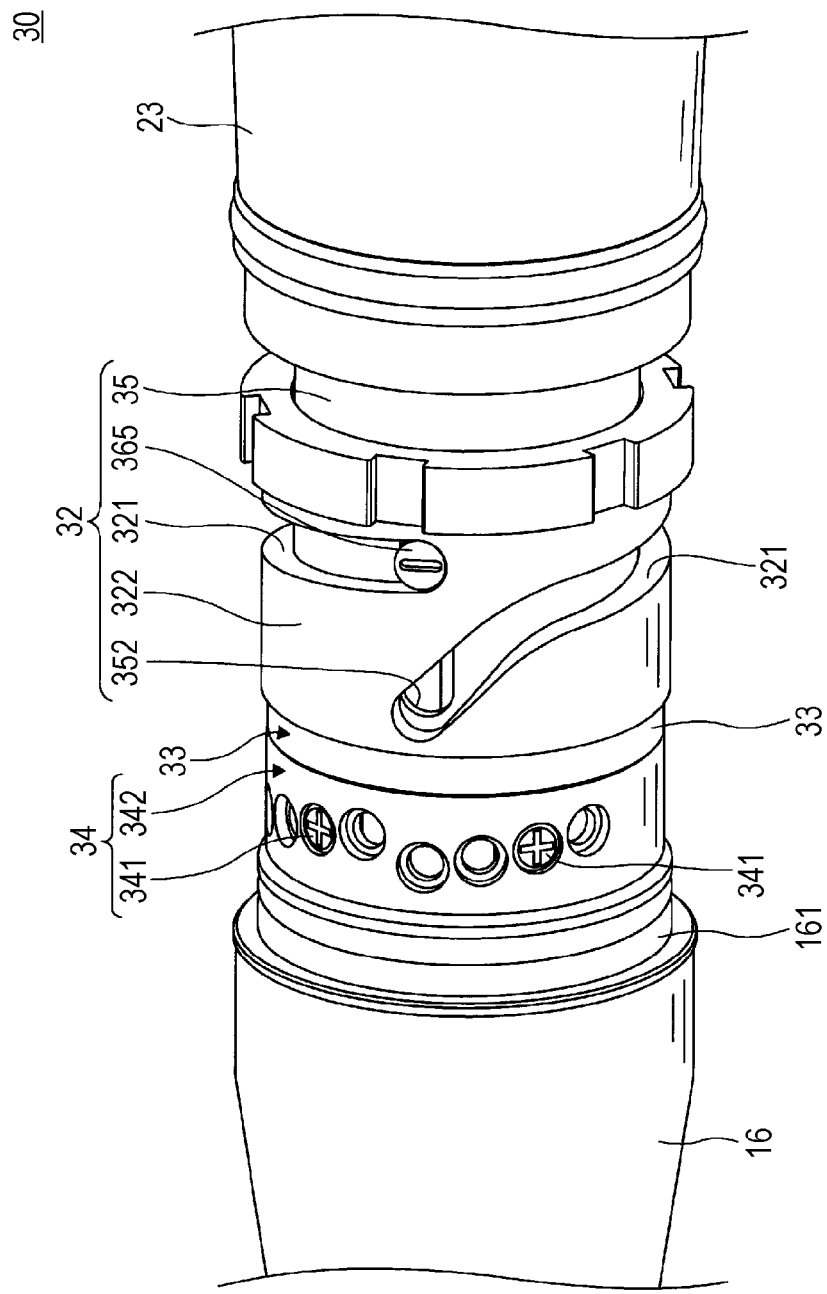
FIG. 16 is an enlarged perspective view of the hardness adjustment operation unit from which the hardness adjustment knob has been removed when the hardness adjustment knob is rotated to the maximum.
Figure 17:
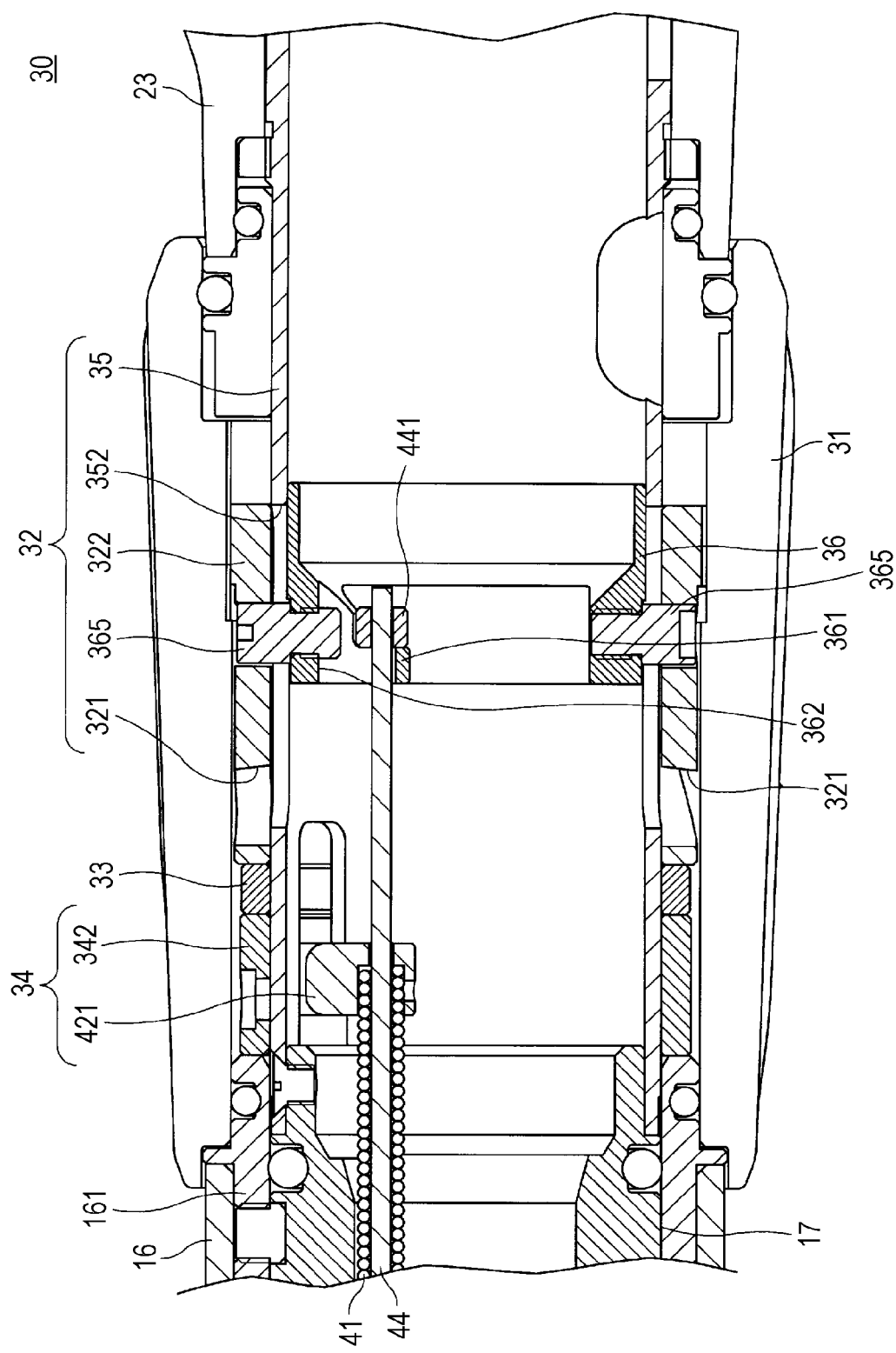
FIG. 17 is a cross-sectional view of the hardness adjustment operation unit when the hardness adjustment knob is rotated to the maximum.

FIG. 16 is an enlarged perspective view of the hardness adjustment operation unit 30 from which the hardness adjustment knob 31 is removed when the hardness adjustment knob 31 is rotated to the maximum. FIG. 17 is a cross-sectional view of the hardness adjustment operation unit 30 when the hardness adjustment knob 31 is rotated to the maximum. The operation of the hardness adjustment mechanism in a process in which the user rotates the hardness adjustment knob 31 from a state illustrated in FIGS. 3 and 10 to a state illustrated in FIGS. 16 and 17 will be described.

When the insertion portion 14 has no flexures and the hardness adjustment cable 40 is not pulled into the insertion portion 14, there is a gap between the sheath fixing ring 342 and the bend preventing cap 161 as illustrated in FIG. 10. When the cam ring 322 starts to rotate, the cam pin 365 moves in the first cam groove 321 so that the cam ring 322 moves to the distal tip side. The cam ring 322 pushes the collar ring 33 and the sheath fixing unit 34 to the distal tip side.

When the sheath fixing unit 34 is pushed to the distal tip side, the coupling tool 46 moves to the distal tip side to pull the hardness adjustment wire 44. The retaining member 441 slides to the distal tip side. The coupling tool 46 pushes the connecting cable 42 to the distal tip side, and the distal tip locking tool 47 slides within the range of the length A described with reference to FIG. 4. The distal tip locking tool 47 stops in a state in which the locking protrusion 471 abuts against a bottom of the receiving groove 129.

On the other hand, in a state in which the insertion portion 14 has many flexures and the hardness adjustment cable 40 is pulled into the insertion portion 14, the sheath fixing ring 342 slides to the distal tip side as illustrated in FIG. 11. As described above, there is the gap that allows the collar ring 33 to move in the axial direction. When the cam ring 322 starts to rotate, the cam pin 365 moves in the first cam groove 321 so that the cam ring 322 moves to the distal tip side. The cam ring 322 pushes the collar ring 33 toward the sheath fixing unit 34.

As described above, the cam ring 322 starts rotating with a relatively small force regardless of whether the insertion portion 14 has a few flexures or many flexures. That is, the user can start to operate the hardness adjustment knob 31 with a relatively small force. Therefore, it is possible to provide the endoscope 10 that does not make the user feel uneasy about whether the hardness adjustment knob 31 is correctly grasped and operated.

The sheath fixing ring 342, the collar ring 33, and the cam ring 322 abut against the bend preventing cap 161. Thereafter, the cam pin 365 and the driven body 36 move to the operation unit side by the first cam groove 321 and the second cam groove 352 when the user turns the hardness adjustment knob 31. After the retaining member 441 abuts against the wire holding portion 361, the hardness adjustment wire 44 is pulled to the operation unit side via the retaining member 441.

As the hardness adjustment wire 44 is pulled to the operation unit side, the coupling tool 46 and the connecting cable 42 are pulled to the operation unit side. The distal tip locking tool 47 slides to the operation unit side within the range of the length A described with reference to FIG. 4. The distal tip locking tool 47 stops in a state in which the locking protrusion 471 abuts against a bottom of the locking tool groove 481.

As described above, the endoscope 10 has abutment portions at three places of the abutment of the distal tip locking tool 47 against the bottom of the locking tool groove 481, the abutments of the sheath fixing ring 342, the collar ring 33, and the cam ring 322 against the bend preventing cap 161, and the abutment of the retaining member 441 against the wire holding portion 361. The order of occurrence of the abutments at the three places changes depending on various conditions such as an assembled state of the hardness adjustment cable 40 and a flexure state of the insertion portion 14. However, when the user rotates the hardness adjustment knob 31 more than a certain level, the abutments occur at all the three places.

When the user further turns the hardness adjustment knob 31 in the state in which the abutments occur at all the three places, the hardness adjustment wire 44 and the coupling tool 46 are pulled to the operation unit side by the cam mechanism 32, the driven body 36, and the retaining member 441.

The sheath fixing ring 342 and the collar ring 33 are sandwiched between the bend preventing cap 161 and the cam ring 322, and thus, do not move. Therefore, the hardness adjustment sheath 41 is compressed between the sheath fixing unit 34 and the coupling tool 46. As a compressive force is applied to the hardness adjustment sheath 41, the hardness of the soft portion 11, more specifically, the hardness of the hardness changing portion 111, which is the portion of the soft portion 11 where the hardness adjustment sheath 41 is arranged, increases.

As described above, the user can increase the hardness of the soft portion 11 by turning the hardness adjustment knob 31 clockwise as viewed from the operation unit side. The user can decrease the hardness of the soft portion 11 by turning the hardness adjustment knob 31 counterclockwise as viewed from the operation unit side.

The greater the pulling amount of the hardness adjustment wire 44, the larger a force required for pulling. However, the operation unit side is substantially parallel to the end surface of the cam ring 322 as described above, the amount of movement of the driven body 36 when the cam ring 322 is turned is small in a state close to FIG. 16. Therefore, the user can easily rotate the hardness adjustment knob 31 to the state illustrated in FIG. 16.

In the state illustrated in FIG. 16, the pulling force acts on the cam pin 365 to the distal tip side. However, the first cam groove 321 is substantially in a circumferential direction. Therefore, the cam ring 322 is maintained in the state illustrated in FIG. 16, and the soft portion 11 is maintained in a high hardness state even when the user releases the hardness adjustment knob 31.

According to the present embodiment, it is possible to provide the endoscope 10 in which the hardness adjustment mechanism operates smoothly. Since the three members of the distal tip locking tool 47, the sheath fixing ring 342, and the retaining member 441 can move freely until the respective abutments, the compression of the hardness adjustment sheath 41 hardly occurs only by the flexure of the insertion portion 14. Therefore, it is possible to provide the endoscope 10 in which the change in the hardness of the soft portion 11 is unlikely to occur when the user does not operate the hardness adjustment knob 31.

According to the present embodiment, the gap that enables the collar ring 33 to move freely is secured, and thus, it is possible to provide the endoscope 10 in which the user can start to operate the hardness adjustment knob 31 with a small force. The user can operate the hardness adjustment mechanism with ease without taking his/her eyes off an endoscopic image.

According to the present embodiment, the cam ring 322 rotates smoothly since the collar ring 33 has high slidability. Therefore, it is possible to provide the endoscope 10 in which the user can operate the hardness adjustment knob 31 without discomfort.

According to this embodiment, the length of the hardness changing portion 111 can be determined by appropriately selecting the lengths of the connecting cable 42, the hardness adjustment sheath 41, and the hardness adjustment wire 44. Therefore, it is possible to provide a lineup of the endoscopes 10 provided with the hardness changing portions 111 having lengths according to applications without changing other constituent members.

Second Embodiment

The present embodiment relates to an endoscope 10 in which a hardness adjustment wire 44 also serves as a connecting cable 42. Descriptions regarding common portions with the first embodiment will be omitted.

Figure 18:
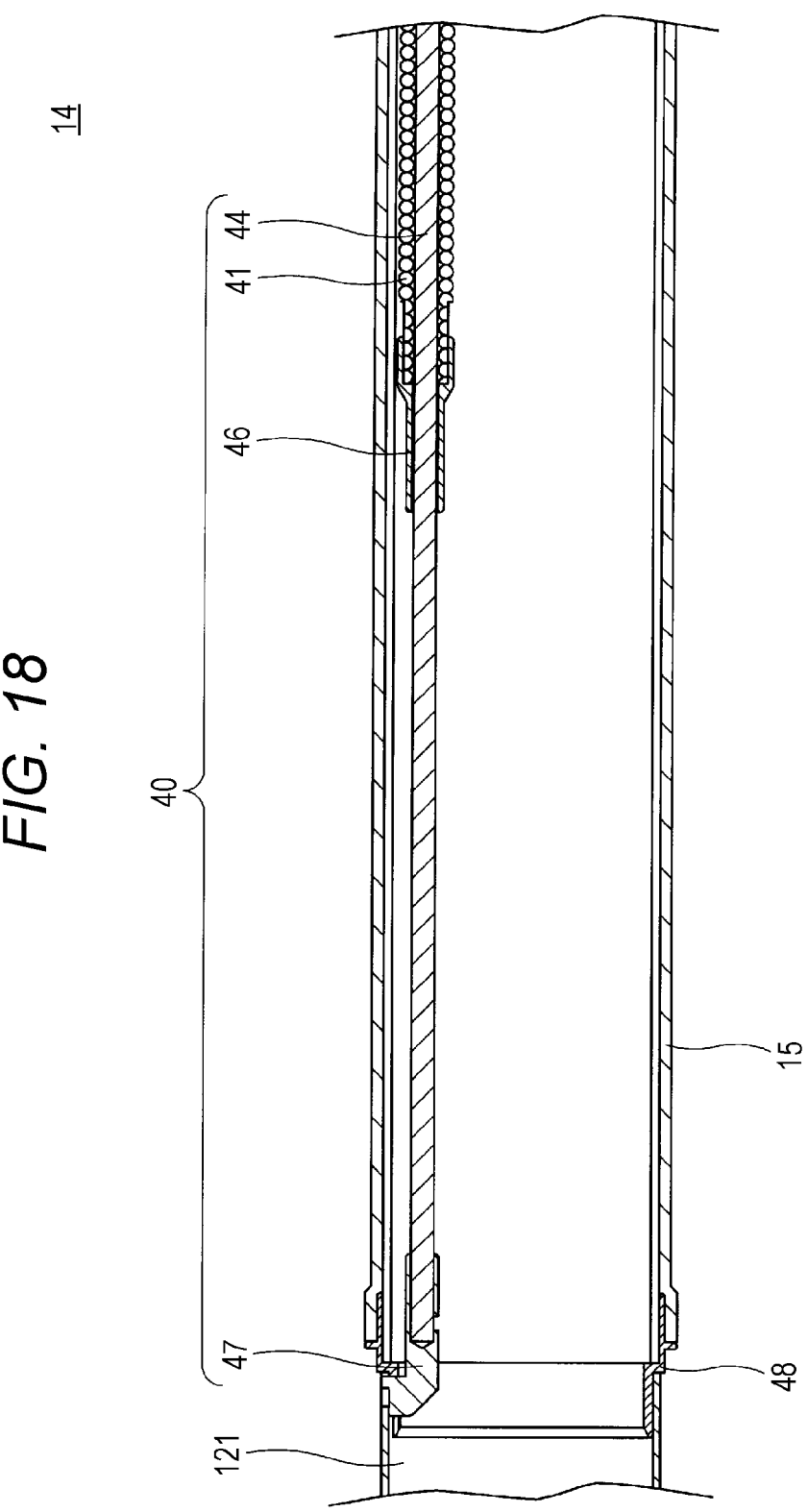
FIG. 18 is a partial cross-sectional view of an insertion portion according to a second embodiment.

FIG. 18 is a partial cross-sectional view of an insertion portion 14 according to a second embodiment. FIG. 18 illustrates a cross section similar to that of FIG. 2. In the present embodiment, the hardness adjustment wire 44 penetrates a coupling tool 46. The coupling tool 46 is fixed to an end portion of a hardness adjustment sheath 41 and the hardness adjustment wire 44. A distal tip locking tool 47 is fixed to an end portion of the hardness adjustment wire 44.

According to the present embodiment, a portion of the hardness adjustment wire 44 on the distal tip side of the coupling tool 46 functions as the connecting cable 42, and thus, the number of parts constituting the hardness adjustment cable 40 can be reduced.

Technical features (constitutional requirements) described in the respective embodiments can be combined with each other, and new technical features can be formed with the combination.

The embodiments disclosed herein are exemplary in all respects, and it should be considered that the embodiments are not restrictive. The scope of the present invention is defined not by the above-described meaning but by claims, and is intended to include all modifications within meaning and a scope equivalent to the claims.

REFERENCE SIGNS LIST

10 Endoscope
11 Soft portion
111 Hardness changing portion
12 Bending section
121 Bending piece
129 Receiving groove
13 Distal tip
14 Insertion portion
15 Exterior tube
16 Bend preventing portion
161 Bend preventing cap
17 Rear end cap
20 Operation unit
21 Bending knob
22 Channel inlet
23 Operation unit housing
25 Universal cord
30 Hardness adjustment operation unit
31 Hardness adjustment knob
32 Cam mechanism
321 First cam groove
322 Cam ring
325 Knob engagement groove
326 Knob engagement portion
33 Collar ring
34 Sheath fixing unit
341 Fixing screw
342 Sheath fixing ring
345 Adjustment hole
35 Guide frame
352 Second cam groove
355 Slide groove
36 Driven body
361 Wire holding portion
362 Wire hole
363 Wire slit
365 Cam pin
40 Hardness adjustment cable
41 Hardness adjustment sheath
42 Connecting cable
421 Sheath receiver
425 Fixing screw hole
44 Hardness adjustment wire
441 Retaining member
46 Coupling tool
47 Distal tip locking tool
471 Locking protrusion
475 Fixing hole
48 Connecting pipe
481 Locking tool groove

The invention claimed is:

1. An endoscope comprising:
a hardness adjustment cable that is arranged in an insertion portion and includes a hardness adjustment sheath, a hardness adjustment wire inserted in the hardness adjustment sheath, and a coupling tool coupling the hardness adjustment sheath and the hardness adjustment wire;
a retainer fixed to the hardness adjustment wire on an operation unit side of the hardness adjustment cable;
a cam mechanism that is coupled to the retainer when tension is applied to the hardness adjustment wire, the cam mechanism including a cam ring and a driven body that moves in a longitudinal direction of the insertion portion in conjunction with rotation of the cam ring;
a sheath fixing unit coupled to the hardness adjustment sheath on the operation unit side of the hardness adjustment cable, the sheath fixing unit including a sheath receiver fixed to the hardness adjustment sheath; and
a cylindrical guide frame that is arranged between the insertion portion and an operation unit and that holds the cam mechanism and the sheath fixing unit such that the cam mechanism and the sheath fixing unit are independently movable of each other in the longitudinal direction of the insertion portion, wherein:
the guide frame is inserted through the cam ring,
the retainer is coupled to the driven body, and
the sheath fixing unit further includes a sheath fixing ring through which the guide frame is inserted and to which the sheath receiver is fixed.

2. The endoscope according to claim 1, further comprising
a collar ring which is arranged between the cam ring and the sheath fixing ring and through which the guide frame is inserted.

3. The endoscope according to claim 2, wherein
the collar ring is made of resin.

4. The endoscope according to claim 2, wherein
in a case where the insertion portion is straight,
the collar ring is movable in the longitudinal direction of the insertion portion when the cam mechanism is in a first state which is one end of a range of motion of the cam mechanism, and the collar ring is immovable in the longitudinal direction of the insertion portion when the cam mechanism is in a second state which is another end of the range of motion of the cam mechanism.

5. The endoscope according to claim 1, wherein the hardness adjustment cable has a connecting cable connected to the coupling tool and extending to a distal tip side of the insertion portion.

6. The endoscope according to claim 5, wherein the hardness adjustment sheath is a coil, and the connecting cable is a coil having an outer diameter smaller than that of the hardness adjustment cable.

7. The endoscope according to claim 5, wherein a tensile rigidity of the connecting cable is lower than a tensile rigidity of the hardness adjustment sheath.

8. The endoscope according to claim 1, further comprising:

a distal tip locking tool coupled to an end portion of the hardness adjustment cable; and a distal tip holding portion that is provided in the insertion portion and holds the distal tip locking tool.

9. The endoscope according to claim 8, wherein the distal tip holding portion holds the distal tip locking tool so as to be movable in the longitudinal direction of the insertion portion.

10. The endoscope according to claim 9, wherein the insertion portion includes a soft portion, a bending section having a plurality of bending pieces, and a connecting pipe connecting the soft portion and the bending section, the distal tip locking tool has a locking protrusion that protrudes toward an outer peripheral side of the insertion portion, the connecting pipe has, on a side surface, a locking tool groove which is open toward the bending section and into which the locking protrusion is inserted, a bending piece of the plurality of bending pieces adjacent to the connecting pipe has a receiving groove, which is open toward the connecting pipe, in a portion corresponding to the locking tool groove on the side surface, and the distal tip holding portion is formed by a portion where the locking tool groove and the receiving groove overlap.

* * * * *